United States Patent
Abe et al.

(10) Patent No.: US 6,903,761 B1
(45) Date of Patent: Jun. 7, 2005

(54) ELECTRONIC ENDOSCOPE SYSTEM ALLOWING ACCURATE DELAY TIME TO BE SET

(75) Inventors: Kazunori Abe, Omiya (JP); Mitsuru Higuchi, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 914 days.

(21) Appl. No.: 09/599,022

(22) Filed: Jun. 21, 2000

(30) Foreign Application Priority Data

Jun. 24, 1999 (JP) .......................................... 11-178440

(51) Int. Cl.⁷ ................................................ H04N 7/18
(52) U.S. Cl. ............................ 348/65; 348/61; 348/77
(58) Field of Search ............................ 348/65, 61, 72, 348/77, 615; 396/17; 600/436

(56) References Cited

U.S. PATENT DOCUMENTS 4,291,961 A * 9/1981 Takayama .................... 396/17
4,807,025 A * 2/1989 Eino et al. .................... 348/72
5,331,961 A * 7/1994 Inaba et al. .................. 600/436

FOREIGN PATENT DOCUMENTS

JP         03118023         5/1991

* cited by examiner

*Primary Examiner*—Allen Wong
(74) *Attorney, Agent, or Firm*—Ronald R. Snider; Snider & Associates

(57) ABSTRACT

This application provides an electronic endoscope system allowing an accurate delay time corresponding to a length of an electronic scope to be set and allowing a configuration to be simplified. The electronic endoscope system is configured by connecting electronic endoscopes different in length to a processor unit and provided with a reference-delay-time generation circuit for generating a signal having a rough reference delay time and a short-delay-time generation circuit for generating a signal having a delay time shorter than the reference delay time by using a gate delay device or the like. A microcomputer in the processor unit reads delay-time-designation control data $D_1$ and $D_2$ from a ROM in an electronic scope, generates a delay drive clock signal by the two delay-time generation circuits in accordance with the control data $D_1$ and $D_2$, and executes preferable image processing in accordance with the delay signal.

4 Claims, 4 Drawing Sheets

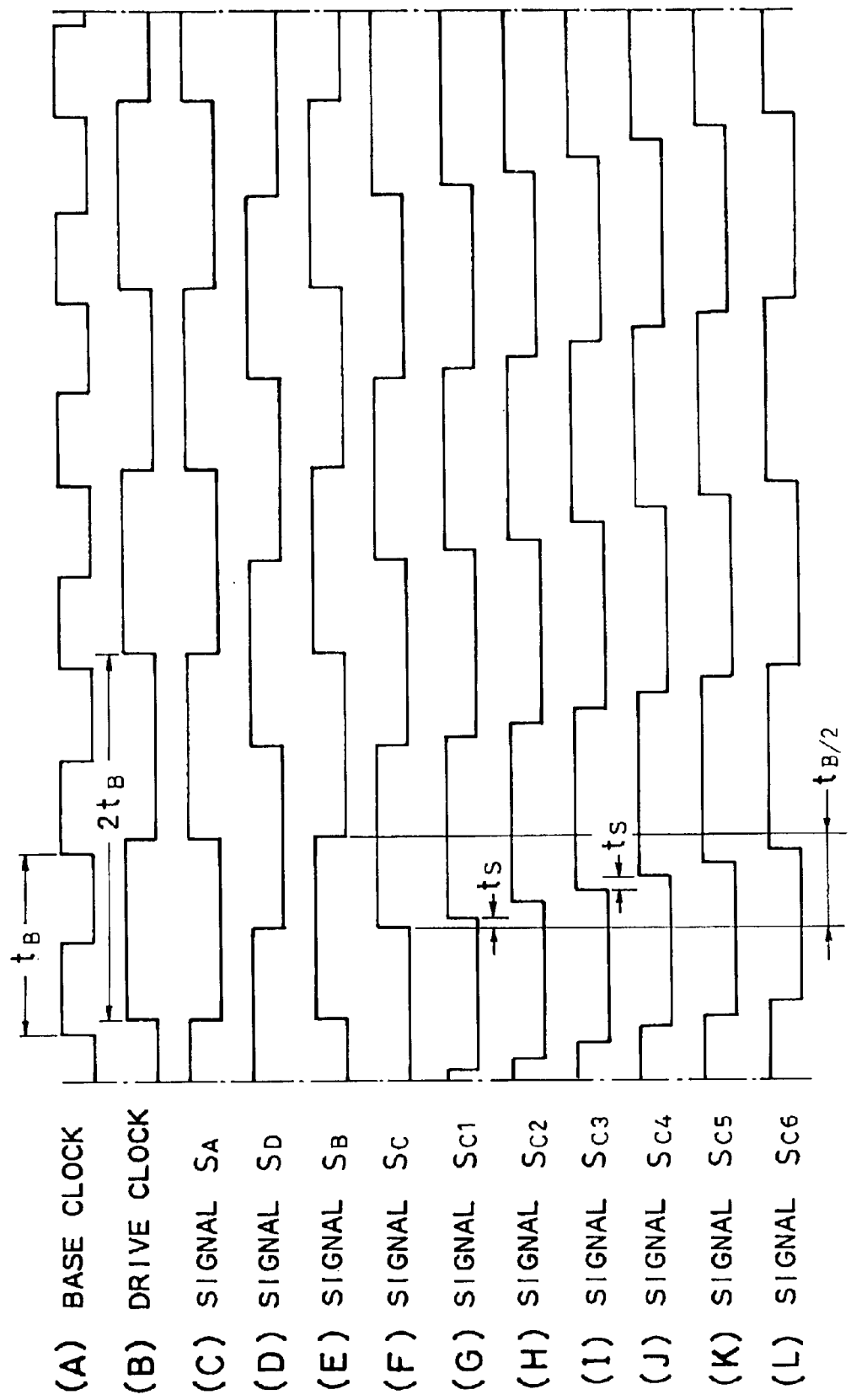

ELECTRONIC ENDOSCOPE SYSTEM ALLOWING ACCURATE DELAY TIME TO BE SET

BACKGROUND OF THE INVENTION

1. Field of the Invention

The present invention relates to an electronic endoscope system, particularly to a configuration for canceling a shift of processing timing of a video signal transmitted from an imaging device at the time of using electronic endoscopes different in length by connecting them.

2. Description of the Prior Art

An electronic endoscope system is configured by connecting various electronic endoscopes different in observation object to a processor unit for executing image processing. Because these electronic scopes are different in length (including cable length), the processor unit provides a delay time corresponding to the length of an electronic scope for a processing signal in order to adjust processing timing correspondingly to a transmission time of a video signal. Japanese Patent Application of Laid-Open Publication No. 03118023A discloses a conventional system for setting and controlling the delay time.

The system of this patent detects scope discriminating information and provides a delay time corresponding to a length of a previously-known electronic scope through tap selection of multitap delay in accordance with the information. In case of a custom electronic scope, a manual adjustment mechanism using a variable resistance is used so as to manually change delay times. As a result, it is possible to correspond to most electronic endoscopes different in length.

BRIEF SUMMARY OF THE INVENTION

Object of the Invention

However, a multitap delay circuit used for the above conventional electronic endoscope system has problems that it can only correspond to a preset delay time, delay times which can be set are rough, and an accurate delay time cannot be set.

Moreover, setting an adjustment circuit using a variable resistance together with a multitap delay circuit requires adjustment and handling becomes complex because the adjustment must be performed every connection between a conventional scope and a new scope.

Summary of the Invention

The present invention is made to solve the above problems and its object is to provide an electronic endoscope system making it possible to set an accurate delay time corresponding to a length of an electronic scope and moreover simplify the configuration.

To attain the above object, the present invention comprises an electronic endoscope to whose front end an imaging device is set, a processor unit connected with the electronic endoscope to apply a predetermined signal processing to a video signal output from the imaging device, a reference-delay-time generation circuit for generating a signal having a rough reference delay time, a short-delay-time generation circuit for generating a signal having a delay time shorter than a reference delay time of the reference-delay-time generation circuit, and a control circuit for generating a delay signal corresponding to the length of the electronic endoscope in cooperation with the delay-time generation circuit and controlling image processing in accordance with the delay signal.

The above short-delay-time generation circuit has a plurality of gate delay devices and makes it possible to set a short delay time in accordance with a delay of a signal passing through the gate delay devices.

According to the above configuration, by supplying delay-time control data obtained from the electronic endoscope to the reference-delay-time generation circuit and the short-delay-time generation circuit, two delay times generated by the delay-time generation circuits are designated and selected and a value obtained by two delay times is set as a delay time. It is possible to set an accurate delay time by a simple configuration in accordance with the combination and cooperation of these two generation circuits.

The above control circuit has a first multiplexer for selecting any one of a plurality of drive clock signals respectively having a reference delay time and a second multiplexer for selecting any one of a plurality of drive clock signals respectively having a short delay time and makes it possible to obtain a delay signal corresponding to the length of the above electronic endoscope by controlling these multiplexers.

BRIEF DESCRIPTION OF THE DRAWINGS

FIG. 4 is a signal waveform diagram showing operations of an embodiment.

DETAILED DESCRIPTION OF THE PREFERRED EMBODIMENTS

Figure 1:
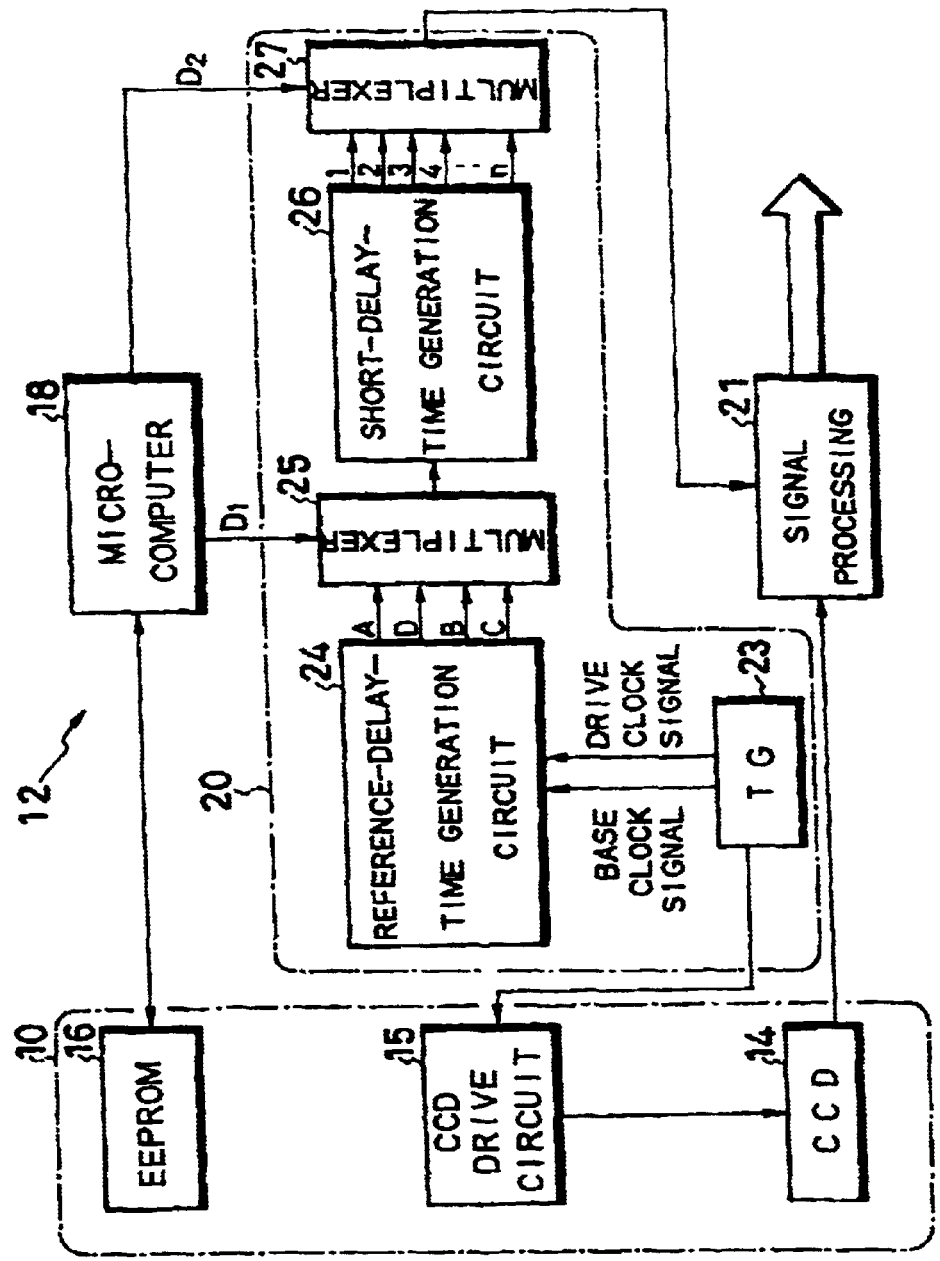
FIG. 1 is a block diagram showing a configuration of an electronic endoscope system of an embodiment of the present invention.
Figure 2:
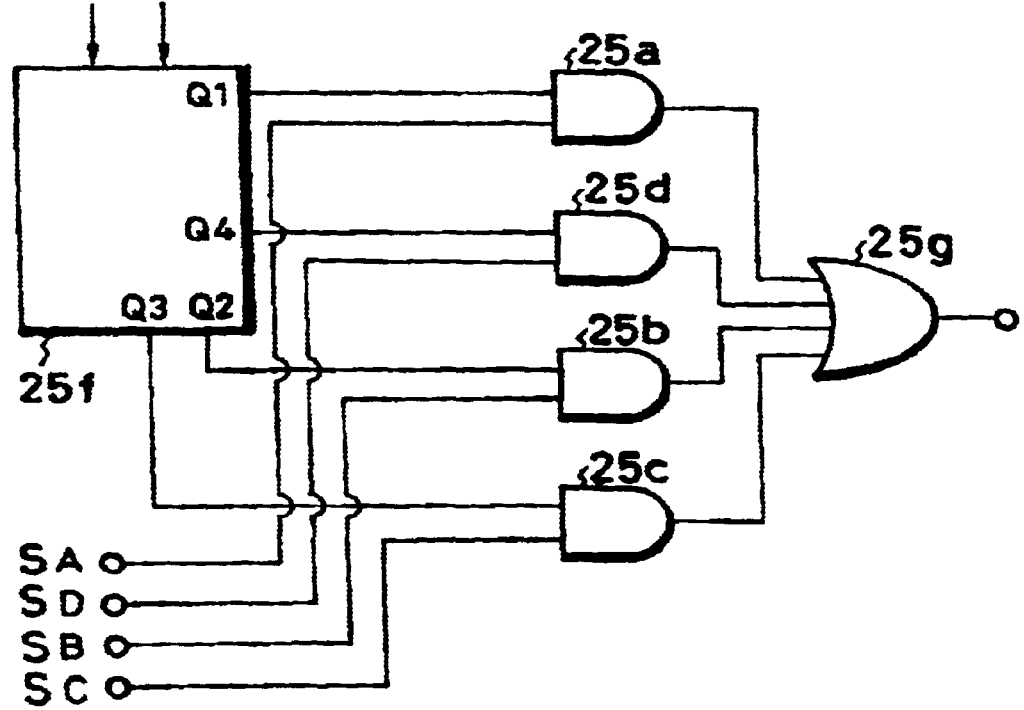
FIG. 2 is a circuit diagram showing a configuration of a multiplexer of an embodiment.
Figure 3:
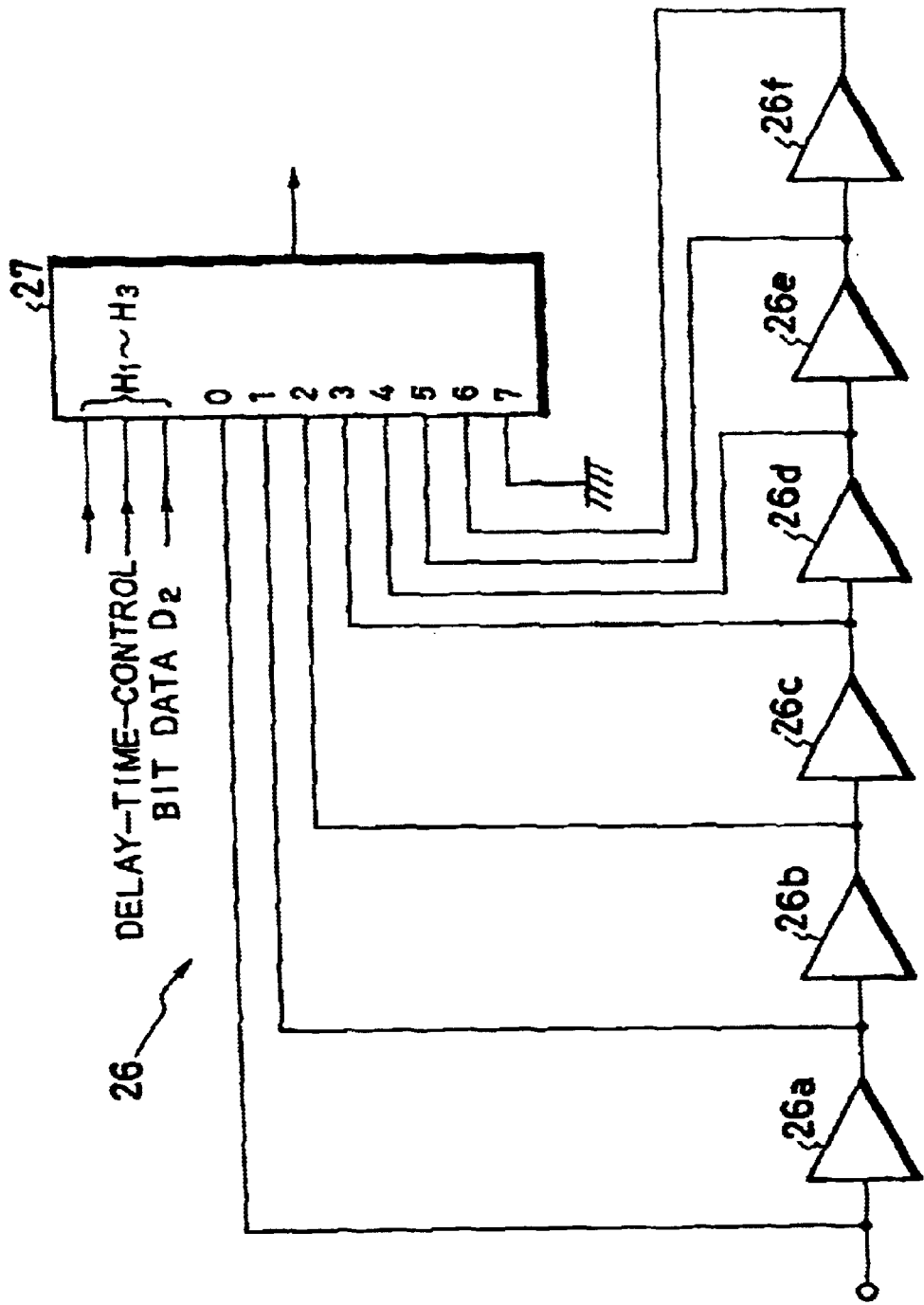
FIG. 3 is a circuit diagram showing a configuration of a short-delay-time generation circuit and a multiplexer of an embodiment.

FIGS. 1 to 3 show a configuration of an electronic endoscope system of an embodiment. As shown in FIG. 1, an electronic endoscope (electronic scope) 10 is configured by connecting with a processor unit (this unit may include a light-source unit) 12. A CCD (Charge Coupled Device) 14 is set to the front end of the electronic scope 10 and a CCD drive circuit 15 is provided to read a video signal from the CCD 14.

Moreover, the electronic scope 10 is provided with a ROM (Read Only Memory such as EEPROM) 16 for storing various pieces of information by being connected with the processor unit 12 to read a video signal and process an image and control data having a delay time corresponding to the length of the electronic scope 10 is stored in the ROM 16. This embodiment stores bit data for directly designating a delay time of each of delay-time generation circuits (24 and 26) to be mentioned later.

The processor unit 12 is provided with a microcomputer 18 for reading data from the ROM 16 and generally controlling circuits in the unit and moreover provided with a timing-signal generation section 20 for generating a timing signal (drive clock signal) to be supplied to the CCD drive circuit 15 and a timing signal (drive clock signal) having a predetermined delay time and a signal processing circuit 21 for image-processing a video signal input from the CCD 14.

The timing-signal generation section 20 includes a timing generator (TG) 23 for generating a base clock signal and a drive clock signal, a reference-delay-time generation circuit 24 for generating a drive clock signal to which a rough delay time is supplied from the base clock signal and drive clock signal, and a multiplexer 25 for selecting a signal obtained by the generation circuit 24 in accordance with the control data sent from the microcomputer 18.

FIG. 2 shows an internal configuration of the multiplexer 25 which is configured of a logic-arithmetic circuit for selecting a delay-time with two-bit control data (the number of bits increases in accordance with the number of selections) 25f, AND circuits 25a, 25d, 25b, and 25c, and an OR circuit 25g. That is, when it is assumed that four drive clock signals $S_A$, $S_D$, $S_B$, and $S_c$ respectively having a rough delay time are generated by the reference-delay-time generation circuit 24 and control data $D_1$ for which a two-bit delay time is supplied to the logic-arithmetic circuit 25f from the microcomputer 18, any one of outputs $Q_1$ $Q_2$, $Q_3$, and $Q_4$ becomes High in accordance with the data $D_1$. For example, when the output $Q_1$ becomes High, the reference-delay-time signal (drive clock signal) $S_A$ is output through the AND circuit 25a and OR circuit 25g. When the output $Q_2$ becomes High, the reference-delay-time signal $S_D$ is output through the AND circuit 25d and OR circuit 25g.

Moreover, a short-delay-time generation circuit 26 and a multiplexer 27 are set to the rear stage of the multiplexer 25 shown in FIG. 1 and details of these circuits are shown in FIG. 3. In FIG. 3, six gate delay devices 26a, 26b, 26c, 26d, 26e, and 26f comprising a CMOS transistor or the like are provided for the short-delay-time generation circuit 26 and outputs of the gate delay device 26a to 26f are connected to input ports 1 to 6 of the multiplexer 27.

The gate delay devices 26a to 26f delay a signal by a time (minimum time is nano-order) for the signal to pass through a transistor device and thereby, set a delay time shorter than the reference delay time, and output six drive clock signals different in delay time in this case. The number of gate delay devices 26a to 26f is optionally set in accordance with the relation between a delay time of a transistor device used and the reference delay time. In the case of this embodiment, fewer gate delay devices are set in order to simplify description.

Moreover, an internal configuration of the multiplexer 27 is basically the same as that in FIG. 2, in which three-bit delay-time control data (the number of bits increases in accordance with the number of selections) $D_2$ supplied from the microcomputer 18 is input from ports $H_1$, $H_2$, and $H_3$ to select six drive clock signals whose short delay times are given from the control data $D_2$.

This embodiment has the above configuration and its functions will be described by referring to FIGS. 4A to 4L. FIGS. 4A and 4B show a base clock and a drive clock output from the timing generator 23 in FIG. 1. A cycle of the drive clock of this embodiment is set to a value two times ($2t_B$) larger than the cycle $t_B$ of the base clock. The reference-delay-time generation circuit 24 generates drive clock signals $S_A$, $S_D$, $S_B$, and $S_c$ having reference delay times shifted from each other every ½ ($t_b/2$) the base clock cycle $t_B$ through logical operation as shown in FIGS. 4C to 4F.

In the short-delay-time generation circuit 26, six drive clock signals having a shift of a short delay time $t_s$ passing through one device are generated by the gate delay devices 26a to 26f. For example, when selecting the signal $S_c$ in FIG. 4F obtained by the reference-delay-time generation circuit 24, drive clock signals $S_{C1}$, $S_{C2}$, $S_{C3}$, $S_{C4}$, $S_{C5}$ and $S_{C6}$ shifted by a short delay time $t_s$ are generated by selecting the input ports 1 to 6 of the multiplexer 27 in FIG. 3 as shown in FIGS. 4G to 4L. Moreover, six signals are similarly generated for other reference-delay-time signals $S_A$, $S_B$, and $S_D$.

When the electronic scope 10 is connected to the processor unit 12 having the timing-signal generation circuit 20, any one of the reference-delay-time signals $S_A$, $S_B$, $S_C$, and $S_D$ is obtained when the microcomputer 18 obtains control data (directly designated data) $D_1$ and $D_2$ for delay times from the ROM 16 and supplies two-bit control data $D_1$ to the reference-delay-time generation circuit 24. Moreover, by supplying three-bit control data $D_2$ to the short-delay-time generation circuit 26, a delay signal more accurately set than the reference delay time is obtained. For example, when the control data $D_1$ for selecting the signal $S_C$ and the control data $D_2$ for selecting the input port 3 (multiplexer 27) are input, the drive clock signal in FIG. 4I is output as a delay signal.

At the time of selecting the port 0 of the multiplexer 27 in FIG. 3, any one of the reference-delay-time signals $S_A$, $S_B$, $S_C$, and $S_D$ is output as a delay signal. Moreover, the delay drive clock signal is supplied to the signal processing circuit 21 and thereby, image processing considering the length of each electronic scope 10 is preferably executed. Thus, this embodiment has an advantage that a delay time can be accurately set by a simple configuration by combining a circuit for generating a rough delay time with a circuit for generating a short delay time.

Moreover, this embodiment is configured so as to directly read designated data for a scope delay time stored in the ROM 16 of the electronic scope 10. However, when only scope ID data is written, it is also permitted that the microcomputer 18 judges a delay time in accordance with ID data so as to generate a predetermined delay-time signal.

Furthermore, by reversing positions of the reference-delay-time generation circuit 24 and short-delay-time generation circuit 26, it is possible to generate a delay signal similarly to the above case.

According to the above configuration, it is possible to set an accurate delay time corresponding to a length of an electronic scope by a simple configuration.

What is claimed is:

1. An electronic endoscope system comprising:
    an electronic endoscope to whose front end an imaging device is set;
    a processor unit connected with the electronic endoscope to apply a predetermined signal processing to a video signal output from the imaging device;
    a reference-delay-time generation circuit for generating a signal having a rough reference delay time;
    a short-delay-time generation circuit for generating a signal having a delay time shorter than a reference delay time of the reference-delay-time generation circuit; and
    a control circuit for generating a delay signal corresponding to a length of the electronic endoscope in cooperation with these delay-time generation circuits and controlling image processing in accordance with the delay signal.

2. The electronic endoscope system according to claim 1, wherein
    the short-delay-time generation circuit is provided with a plurality of gate delay devices to set a short delay time according to a delay of a signal passing through the gate delay devices.

3. The electronic endoscope system according to claim 1, wherein
    the control circuit has a first multiplexer for selecting any one of a plurality of drive clock signals generated by the reference-delay-time generation circuit and respectively having a reference delay time and a second multiplexer for selecting any one of a plurality of drive clock signals respectively generated by the short-delay-time generation circuit and respectively having a short delay time, and a delay time corresponding to the length of the electronic endoscope is obtained by controlling the first and second multiplexers.

4. The electronic endoscope system according to claim 1, wherein the control circuit is set to a processor unit, reads delay-time data for a connected electronic endoscope from the electronic endoscope, and generates a necessary delay signal in accordance with the delay-time data.

\* \* \* \* \*